US007041464B2

(12) United States Patent
Haikara et al.

(10) Patent No.: US 7,041,464 B2
(45) Date of Patent: May 9, 2006

(54) METHOD FOR DETERMINING A GUSHING FACTOR FOR A BEVERAGE

(75) Inventors: Auli Haikara, Helsinki (FI); Tuija Kleemola, Helsinki (FI); Tiina Nakari-Setälä, Espoo (FI); Merja Penttilä, Helsinki (FI)

(73) Assignee: Panimolaboratorio-Bryggerilaboratorium, Espoo (FI)

( * ) Notice: Subject to any disclaimer, the term of this patent is extended or adjusted under 35 U.S.C. 154(b) by 56 days.

(21) Appl. No.: 10/920,832

(22) Filed: Aug. 18, 2004

(65) Prior Publication Data

US 2005/0014204 A1  Jan. 20, 2005

Related U.S. Application Data

(63) Continuation of application No. 10/309,911, filed on Dec. 4, 2002, now abandoned, which is a continuation-in-part of application No. 09/673,460, filed as application No. PCT/FI99/00305 on Apr. 4, 1999, now abandoned.

(30) Foreign Application Priority Data

Apr. 17, 1998 (FI) ...................................... 980863

(51) Int. Cl.
*G01N 33/53* (2006.01)
(52) U.S. Cl. .......................... 435/7.31; 435/4; 435/7.1; 435/7.2; 435/7.92; 435/803; 435/812; 436/518; 436/161; 436/815
(58) Field of Classification Search ................ 435/4, 435/7.1–7.2, 7.31–7.32, 7.9, 7.92, 803, 812, 435/814; 436/161, 164, 518, 536, 805, 815; 530/300, 350, 370–371, 823
See application file for complete search history.

(56) References Cited

U.S. PATENT DOCUMENTS

| 6,080,405 A | 6/2000 | Ishibashi et al. | .......... 424/141.1 |
|---|---|---|---|
| 6,103,468 A | 8/2000 | Russell et al. | .................. 435/6 |
| 6,368,876 B1 * | 4/2002 | Huang et al. | ................ 436/518 |

OTHER PUBLICATIONS

Dialog Information Services, File 5, Biosis Previews, Dialog Accession No. 11609030, Biosis No. 199803390792, Kakui T. et al.: Development of Monoclonal Antibody Sandwich-Elisa for Determination of Beer Foam-Active Proteins; Journal of the American Society of Brewing Chemists 56 (2): pp. 43-46, 1998.
Dialog Information Services, File 5, Biosis Previews, Dialog Accession No. 10801781, Biosis No. 199799422926, Ishibashi Y(a) et al.: Application of Elisa to Quantitative Evaluation of Foam-Active Protein in the Malting and Brewing Processes; & Journal of the American Society of Brewing Chemists 55 (1):pp. 20-23, 1997.
Dialog Information Services, File 5, Biosis Previews, Dialog Accession No. 11783307, Biosis No. 199900029416, Mills E N Clare(a) et al: Immunlological Study of Hydrophobic Polypeptides in Beer; & Journal of Agricultural and Good Chemistry 46 (11): pp. 4475-4483, 1998.
Trends in Plant Science, vol. 1, No. 1, Jan. 1996, Joseph G.H. Wessels, Fungal hydrophobins: proteins that function at an interface; pp. 9-15.
European Brewery Convention Proceedings of the 24th Congress, 1993, Pia Vaag et al: Practical experiences with immunological detection of Fusarium in barley and malt, pp. 111-120; p. 113, lines 1-41; p. 118, line 9 to p. 120, line 28.
Wessels, J.G.H., Hydrophobins: Proteins That Change the Nature of the Fungal Surfaces, Advances in Microbial Physiology, vol. 38, 1997 Academic Press Limited, pp. 1-45.
Vaag, P., Enzyme-Liked ImmunoSorbent/Assay (ELISA) in the Beverage Insutries: Principles and Practice, Analysis of Non-Alcoholic Beverages, Modern Methods of Plant Analysis, new series vol. 8, Eds. Liskens, H.H. and Jackson, J.F., Springer-Verlag Berlin 1988, pp. 1-29.
Vaag, P., Immunological Detection of *Fusarium* in Barley and Malt, Proc. Eur. Brew. Conv. Lisbon 1991, pp. 553-560.
Kakui et al, Development of Monoclonal Antibody Sandwich-Elisa for Determination of Beer Foam-Active Proteins, J. Am. Soc. Brew. Chem. (1998) vol. 57, No. 1, pp. 20-23.
Ishibashi et al, Application of Elisa to Quantitative Evaluation of Foam-Active Protein in the Malting and Brewing Process, J. Am. Soc. Brew. Chem. (1997) vol. 55, No. 1, pp. 20-33.
Haikara, A. Gushing Induced by Fungi, Monogr. Eur. Brew. Conv. (1981), vol. 6, pp. 251-259.
Tenberge et al, Nonradioactive In Situ Hybridization for Detection of Hydrophobin MRNA in the Phytopathogenic Fungus Claviceps Purpurea During Infection of Rye, European Journal of Cell Biology, (Mar. 1998), vol. 75, No. 3, pp. 265-272.
Vaag et al, A Simple and Rpaid Test for Gushing Tendency in Brewing Materials, EBC Congress 1993, pp. 155-162.
Vaag et al, Practical Experiences with Immunological Detection of Fursarium in Barley and Malt, EPC Congress 1993, pp. 111-120.

* cited by examiner

*Primary Examiner*—Long V. Le
*Assistant Examiner*—Leon Y. Lum
(74) *Attorney, Agent, or Firm*—Andrus, Sceales, Starke & Sawall, LLP

(57) ABSTRACT

The invention relates to a method for determining a gushing factor for a beverage, in which method the quantity of hydrophobin is determined from the raw material of the beverage and/or from the beverage. The hydrophobin determination is performed immunologically using an immunological reaction between a hydrophobin antigen and an antibody.

8 Claims, No Drawings

METHOD FOR DETERMINING A GUSHING FACTOR FOR A BEVERAGE

CROSS-REFERENCE TO RELATED APPLICATIONS

This application is a continuation application of U.S. application Ser. No. 10/309,911, filed Dec. 4, 2002 now abandoned, which is a continuation-in-part of U.S. application Ser. No. 09/673,460, filed Nov. 22, 2000 now abandoned, which is the U.S. national stage application of International Application PCT/FI99/00305, filed Apr. 9, 1999, which international application was published on Oct. 28, 1999 as International Publication WO 99/54725 in the English language. The International Application claims priority of Finnish Patent Application 980863, filed Apr. 17, 1998.

BACKGROUND OF THE INVENTION

The present invention relates to a method for determining a gushing factor for a beverage, particularly for beer and other malt beverages.

In beer production, if mould infected barley is used in brewing, the beer produced may be liable to gushing. Gushing is a phenomenon of excessive effervescence of beer, for instance beer may spurt out of a bottle when it is opened. Among the worst factors causing gushing are *Fusarium* moulds, but gushing activity is also observed in moulds of the *Altpnaria, Aspergillus, Nigrospora, Penicillium* and *Stemphylium* species. Research on gushing factors produced by moulds has been carried on for decades, but so far it has not been possible to accurately identify and characterise those factors. It has been established that gushing factors are peptides or at least compounds containing peptides. Moreover, they have been found to be of a hydrophobic and acid nature. The gushing factors of most mould fungi are quite rich in cystein. Recent research gives reason to assume that gushing factors are concentrated in the husks of barley.

SUMMARY OF THE INVENTION

At present, the gushing propensity of beer is tested by determining the proportion of grains infected with *Fusarium* moulds in a batch of barley. The batch is rejected if the proportion of infected grains exceeds an allowed limit. This method is laborious and slow to implement and it is not quantitative. The worst weakness of the method is the fact that it cannot be used to determine a real factor that causes gushing, a gushing factor. Therefore, the results may lead to incorrect conclusions.

The object of the present invention is to eliminate the drawbacks mentioned above.

A specific object of the present invention is to provide a reliable method for determining the gushing propensity of beverages, especially beer, from the raw materials of the beverages, a method that is applicable in quality control. In particular, the object of the method is to determine the amount of a real gushing factor in beer from grain.

The method of the invention is characterised by what is presented in the claims.

DETAILED DESCRIPTION OF THE INVENTION

The invention is based on research work carried out to study the factors causing gushing of beer, during which it was established that hydrophobic proteins, hydrophobins, are gushing factors in beer.

Hydrophobins are small hydrophobic proteins produced by moulds and generally containing e.g. 100±25 amino acids. So far, hydrophobins have been isolated from several mould fungi and edible mushrooms. A feature characteristic of hydrophobins is that they have 8 cystein residues which are located in protein in accordance with a certain formula. Hydrophobins occur on the surface of mould mycelium and spores and in secretions in the substratum. Hydrophobins are agents promoting the attachment of mycocelia to the substratum and to each other and they form a protective layer on the surface of the aerial mycelium and spores, protecting them against becoming waterlogged. It has been established that hydrophobins gather at the interface between phases, e.g. on the surface of air bubbles in a culture solution, forming amphipathic films at the interface. Due to their film forming capability, hydrophobins change the surface properties of materials from hydrophobic to hydrophilic and vice versa. Their ability to reduce the surface tension of a water solution is comparable to that of certain synthetic detergents. Hydrophobins are described e.g. in the following articles: Wessels, J. G. H., Hydrophobins: Proteins that Change the Nature of the Fungal Surface, Advances in Microbial Physiology, vol. 38, 1997 Academic Press Limited, pp. 1–45 and Wessels, J. G. H., Fungal hydrophobins: proteins that function at an interface, Trends in Plant Science, vol. 1, s. 9–15. Hydrophobins stabilise bubbles, causing foaming of the culture solution. It has been established that the hydrophobin now isolated from moulds causes gushing of beer.

According to the invention, the amount of hydrophobin in the raw material of a beverage and/or in a beverage, especially in grains, such as barley, malt and/or beer, can be determined by any method applicable for the determination of hydrophobin.

In a preferred embodiment, hydrophobin is determined immunologically by using an immunological reaction between a hydrophobin antigen and an antibody. The immunological method may be an immunoradiometric, immunoenzymetric, immunofluorometric or immunoluminometric method. The antibodies specific to hydrophobin proteins which are needed in the determination are produced by conventional methods of producing antibodies.

Hydrophobin proteins can be isolated from mould strains having a gushing activity, especially from *Fusarium* strains. Usable strains are e.g. *Gibberella avenacea* (*F.avenaceum*), *F.culmorum, F.poae, Gibberella zeae* (*F.graminearum*), *Nigrospora* sp. and *T.reesei*. Hydrophobins can be isolated from mould mycelium and/or culture solutions by conventional methods e.g. by extracting, bubbling and/or cold drying.

Hydrophobin can be isolated from mycelium by a three-phase extraction method and/or from a culture solution by bubbling the solution, causing concentration of hydrophobin in the foam produced, and/or by deep-freezing the culture solution, causing sedimentation of hydrophobin, which can then be separated by centrifuging the solution after it has been melted.

In a preferred embodiment of the method for determination of hydrophobin, the ELISA (Enzyme Linked ImmunoSorbent Assay) method is used. The colour or fluorescence produced in the enzymatic reaction in the method indicates the presence and quantity of hydrophobin. The ELISA method, the preparation and purification of antibodies and the enzymes, conjugates and substrates used in it are described e.g. in the following article. Vaag, P., Enzyme-Linked ImmunoSorbent Assay (ELISA) in the Beverage Industries: Principles and Practice, Analysis of Non-Alcoholic Beverages (Modern Methods of Plant Analysis, new series vol. 8), Eds. Liskens, H. H. and Jackson, J. F., Springer-Verlag, Berlin 1988, pp. 1–29.

In the method of the invention, other corresponding immunological procedures can also be used, such as the EBStrALISA (Enzyme Biotin Streptavidin Linked ImmunoSorbent Assay) method. The EBStrALISA method is described e.g. in the article Vaag, P., Immunological detection of *Fusarium* in barley and malt, Proc. Eur. Brew. Conv. Lisbon 1991, pp. 553–560.

In a second preferred embodiment of the method, hydrophobin is determined immunochromatographically using a test strip based on immunochromatography. The colour produced in the immunological reaction in the method indicates the presence and quantity of hydrophobin.

The test strip used may comprise e.g. a chromatographic membrane provided with moving marking particles and two stationary hydrophobin antibody areas. The sample is absorbed into the test strip membrane, where it reacts with the marking particles and drifts into the antibody areas on the membrane. If the sample contains hydrophobin, coloured test and control lines will appear in the antibody areas as a result of an immunological reaction. If the sample does not contain any hydrophobin, only a control line will appear.

The invention makes it possible to replace the semi-quantitative detection method based on indication of *Fusarium* fungus as used in industrial quality control with a new reliable precision method when a primary gushing factor is to be determined from the grain. By selecting the grain to be used, especially barley, by the new method, it will be possible to reduce the need for precautions, which have proved to be expensive and inefficient, especially in risk years when grain quality is low and beer produced from such grain shows a strong tendency to gushing.

Further, the new immunological detection method provides a faster and simpler and therefore cheaper method for determining the gushing tendency of barley.

In the following, the invention will be described in detail by means of a few examples.

EXAMPLE 1

Isolation and Indication of Hydrophobins

Hydrophobin was isolated from mould strains having a gushing activity: *Gibberella avenacea* (*F.avenaceum*) (VTT-D-80141), *F.culmorum* (VTT-D-80148), *F.poae* (VTT-D-82182), *Gibberella zeae* (*F.graminearum*) (VTT-D-95470), *Nigrospora* sp. (VTT-D-79122) and *T.reesei* (VTT-D-74075).

Moulds were cultivated on three different substrates: on agar, in culture solution and in barley. Hydrophobin was isolated by a three-phase extraction method and by bubbling the culture solution. The molecular distribution of the proteins contained in the sample was established via gel electrophoresis. The hydrophobin produced by the *T.reesei* strain is of a size about 7.5 kDa. The hydrophobins produced by the *Nigrospora* sp. (mycelium extraction) and *F.poae* (bubbling of culture solution) strains were of about the same size. The hydrophobin extracted from the mycelium of the *Gibberella zeae* strain was of a size about 20 kDa.

For the indication of hydrophobins in a sample, the immunological ELISA test was used. The antibody used in the test was prepared using the following immunising protocol. A rabbit was immunised using a hydrophobin produced by *T.reesei* mould, which was mixed with Freund's adjuvant. Injections were given 4 times during three months. Titre development was monitored by determining the antibody content of the blood twice using the ELISA method. At the end of the immunising period, the rabbit's blood was collected and the serum was separated from the blood. The reactivity of the serum was tested by determining the weakest serum dilution that still gives a response in the ELISA method. The dilution was over 1/100 000.

In the test, a hydrophobin sample was pipetted into the pits on a microtitre plate, with the result that the proteins in the sample became attached to the walls of the pits. Hydrophobin antibody was then added, and it recognised the hydrophobin protein on the walls and attached to it. After this, a conjugate was added, which in turn attached to the antibody. The conjugate contained an enzyme which produced colouring of the substrate pipetted into the pits. The intensity of the colour of the substrate was directly proportional to the hydrophobin content of the sample.

The highest responses were obtained from hydrophobin samples of *F.poae*, *Nigrospora* sp. and *T.reesei*.

EXAMPLE 2

Determination of Hydrophobin from a Barley Sample

Barley was subjected to contamination with the *Fusarium* strains and *T.reesei* strain of example 1 for two weeks. A barley extract was prepared by mixing 50 g of barley/100 ml of water for 1 minute. The barley-water mixture was centrifuged for 15 minutes at a velocity of 4000 g. The supernatant extract was collected and the hydrophobin contained in it was determined by the direct ELISA method using an antibody prepared against *T.reesei* hydrophobin.

On microtitre plates, barley extract diluted to 1/10 and 1/100 was pipetted in an amount of 150 µl/pit. The dilutions were prepared in a sodium phosphate buffer (10 mM of sodium phosphate pH 7.3, 150 mM of sodium chloride=PBS solution). The plate was kept in a refrigerator overnight. On the next day, PBS solution containing 0.1% bovine serum albumen and 0.05% Tween 20 solution (=BSA/PBS solution) was pipetted onto the plate in an amount of 100 µl/pit. The plate was held at a low temperature overnight, whereupon it was washed with a PBS solution containing 0.01% Tween 20 solution added to it (PBST solution). From hydrophobin antibody, a 1/100 dilution was made in the BSA/PBS solution. Of this antibody dilution, 100 µl/pit was pipetted onto the plate and the plate was incubated for 2 h at +37° C. The plate was washed with PBST solution. Next, 100 µl/pit of conjugate: goat's anti-rabbit 1 gG alkaline phosphatase diluted to 1/1000 in BSA/PBS solution, was pipetted onto the plate. The plate was incubated for 2 h at +37° C. and washed with PBST solution. Finally, 100 µl/pit of substrate: 1 tablet of p-nitrophenyl phosphate/5 ml of diethylene amine+$MgCl_2$ buffer, was pipetted onto the plate. The plate was incubated in a shaker for 30 min at room temperature. The absorbance was measured at wavelength 405 nm using a Multiscan photometer. The intensity of colour is directly proportional to the amount of hydrophobin contained in the sample table 1 presents the absorbance values of the barley samples.

TABLE 1

| Sample | Sample dilution 1/10 | 1/100 |
|---|---|---|
| Control | 0.551 | 0.388 |
| VTT-D-80141 | 1.823 | 1.360 |
| VTT-D-80148 | 0.452 | 0.374 |
| VTT-D-82182 | 1.088 | 0.898 |
| VTT-D-95470 | 0.664 | 0.634 |
| VTT-D-74075 | 0.863 | 1.914 |

The highest hydrophobin contents were determined from barley samples contaminated with *Gibberella avenacea*, *F.poae* and *T.reesei* mould strains.

The method is also well applicable for use with malt samples.

```
F. poae:
TPPGYGGGGGGSGSNFDA    C    PGALYSQTQ    CC    SAGVGDIVDV...    (Seq. ID No. 1)
i.e.    X18-C-X9-C-C ....

Nigrospora sp.:
TNDQPATGFVA   C   ANNGVLFSAPN   CC   ATDVLGLADLD   C   TTPPKVPTSPXDFQ...   (Seq. ID No. 2)
i.e.    X11-C-X11-C-C-X11-C ...
T = Thr, P = Pro, G = Gly, Y = Tyr, S = Ser, N = Asn, F = Phe, D = Asp,
A = Ala, L = Leu, Q = Gln, V = Val, I = Ile, K = Lys.
```

EXAMPLE 3

Beer Gushing Tests

A beer gushing test was performed by adding 0.5–1 ml of hydrophobin sample into a beer bottle. The bottle was shaken for 3 days at room temperature, whereupon it was opened and the amount of beer gushing out was determined from the change in the weight of the bottle.

The hydrophobin samples of *T.reesei* (mycelium extraction) and *F.poae* (bubbling of culture solution) produced particularly intensive gushing. The gushing in the case of the former sample was even more than 50%, and in the case of the latter sample 30–45%. The hydrophobin sample of *Nigrospora* sp (mycelium extraction) caused repeated gushing of 1–10%. The hydrophobin samples of the other moulds tested also caused gushing of beer in varying degrees.

On the basis of the tests carried out, it can be stated that hydrophobin proteins cause gushing of beer.

EXAMPLE 4

Hydrophobin Sequencing

The hydrophobin samples in Example 1 of *Fusarium poae* (bubbling of culture solution) and *Nigrospora* sp (mycelium extraction) causing gushing of beer were fractionated using the technique of reversed-phase HPLC chromatography (High Performance Liquid Chromatography) (apparatus: Äkta Explorer, Pharmacia Biotech; column: C4, Vydac). The operating buffers used were 0.1% trifluoroacetic acid (TFA) in water (A) and 0.1% TFA in acetonitrile (B). The gradient developed so that operation was started with buffer A and the proportion of buffer B increased in the course of the operation so that finally the operating solution consisted of buffer B only. Proteins like hydrophobin were eluted when the concentration of buffer B was about 50%. From the fractions obtained, a sodium dodecylsulphate-polyacrylamide gel electrophoresis (SDS-PAGE) was made by means of a Phast apparatus (Pharmacia) using 20% Phast gels. On fractions containing hydrophobin-sized proteins, an N-terminal sequence analysis was made. A characteristic of the order of aminoacids in hydrophobins is that there are eight cystein residues located in the protein according to the following formula (Wessels, J. G. H. (1996) Fungal hydrophobins: proteins that function at an interface, Trends in plant science. 1:9–15):

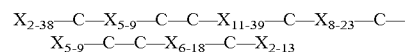

X=aminoacid other than cystein
C=cystein Cys.

For the sample fractions, the following partial N-terminal sequences were obtained:

The sequences for the samples are well in agreement with the sequential formula for hydrophobins. When a sample fraction of *Nigrospora* sp. was added to beer and a gushing test was performed, half of the beer gushed out. Fractions that did not contain any hydrophobin-sized proteins did not produce any gushing.

The invention is not restricted to the examples of its embodiments described above, but many variations are possible within the scope of the inventive idea defined in the claims.

EXAMPLE 5

The Effect of the Addition of Hydrophohins on the Gushing Tendency of Beer

The hydrophobin samples isolated from the growth medium by bubbling or from the mycelium using a 3-stage extraction method were purified using reversed-phase-high pressure-liquid chromatography (RP-HPLC, apparatus: Äkta Explorer, Pharmacia Biotech, column: Vydac C4),). Eluation was performed with linear gradient of acetonitrile in 0.1% trifluoroacetic acid. The partial amino acid sequences of the purified proteins were determined by N-terminal sequence analysis. The protein contents of the purified hydrophobin samples were determined using BC Assay Protein Determination kit (Uptima) or from the HPLC-chromatogram.

The gushing activity of the hydophobin samples were studied by adding a purified sample to the beer and by shaking the bottles in accordance with the modified gushing test instruction for malt (Haikara 1980, Vaag et al., 1993) during three days (50 rpm, plane shaker). The bottles were kept still for 10 minutes before opening them, after which the bottles were turned upside down three times and opened after 30 seconds. The amount of gushing was determined from the change of the weight of the bottle. The results from the gushing test are presented in table 1.

TABLE 1

The effect of the addition of two hydrophobins, HFB I and HFB 2, isolated from *Trichoderma reesei* -fungi (VTT D-74075), and one hydrophobin isolated from *Fusarium poae* -fungi (VTT D-82182) on the gushing tendency of beer.

| Addition | Gushing/g | | |
|---|---|---|---|
| μg/0.33 l beer | *T. reesei* HFBI | *T. reesei* HFBII | *F. poae* |
| 0.01 | 0 | 0 | — |
| 0.1 | 0 | 0 | — |
| 1 | 10 | 12 | 0 |
| 10 | 189 | 192 | 0 |
| 45 | — | — | 27 |
| ~40 | — | — | foam cap |
| ~50 | — | — | 15 |

—: not determined

Haikara, A., Gushing induced by fungi, *Eur. Brew. Conv. Monogr. VI*, Symposium on the relationship between malt and beer, Helsinki 1980, Brauwelt-Verlag Nürnberg, pp. 251–259.

Vaag, P., Riis, P., Knudsen, A.-D., Pedersen, S. and Meiling, E., A simple and rapid test for gushing tendency in brewing materials, *Proc. Eur. Brew. Conv. 24th Congress*, Oslo 1993, IRL Press, pp. 155–162.

As shown above, the minimum detected amount of hydrophobin that results in gushing of the beer is about 1 μg/0.33 liters of beer.

---

The invention claimed is:

1. A method for determining the presence of a factor in a raw material for a beverage indicative of a gushing propensity of the beverage, said method comprising the step of determining a quantity of hydrophobin present in a raw material for a beverage or from the beverage made using said raw material, said hydrophobin having the formula $X_{2-38}$—C—$X_{5-9}$—C—C—$X_{11-39}$—C—$X_{8-23}$—C—$X_{5-9}$—C—C—$X_{6-18}$—C—$X_{2-13}$ where X is an aminoacid other than cysteine, and C is a cysteine residue, and determining whether the quantity of hydrophobin present causes gushing of the beverage.

2. The method of claim 1 wherein the step of determining a quantity of hydrophobin comprises determining a quantity of hydrophobin in barley.

3. The method of claim 1 wherein the step of determining a quantity of hydrophobin comprises determining a quantity of hydrophobin in malt.

4. The method of claim 1 wherein the step of determining a quantity of hydrophobin comprises determining a quantity of hydrophobin in beer.

5. The method of claim 1, wherein the step of determining the hydrophobin quantity is performed using an immunological reaction between a hydrophobin antigen and an antibody.

6. The method of claim 1, wherein the step of determining the hydrophobin quantity is performed using an Enzyme Linked ImmunoSorbent Assay (ELISA) method.

7. The method of claim 1, wherein the step of determining the hydrophobin quantity is performed using an Enzyme Biotin Streptavidin Linked ImmunoSorbent Assay (EBStrALISA) method.

8. The method of claim 1, wherein the step of determining the hydrophobin quantity is performed immunochormatographically.

* * * * *

SEQUENCE LISTING

```
<160> NUMBER OF SEQ ID NOS: 5

<210> SEQ ID NO 1
<211> LENGTH: 40
<212> TYPE: PRT
<213> ORGANISM: F.poae

<400> SEQUENCE: 1

Thr Pro Pro Gly Tyr Gly Gly Gly Gly Gly Ser Gly Ser Asn Phe
1               5                   10                  15

Asp Ala Cys Pro Gly Ala Leu Tyr Ser Gln Thr Gln Cys Cys Ser Ala
            20                  25                  30

Gly Val Gly Asp Ile Val Asp Val
            35                  40

<210> SEQ ID NO 2
<211> LENGTH: 51
<212> TYPE: PRT
<213> ORGANISM: Nigrospora sp
<220> FEATURE:
<221> NAME/KEY: MISC_FEATURE
<222> LOCATION: (48)..(48)
<223> OTHER INFORMATION: Xaa can be any naturally occurring amino acid
      other than cysteine

<400> SEQUENCE: 2

Thr Asn Asp Gln Pro Ala Thr Gly Phe Val Ala Cys Ala Asn Asn Gly
1               5                   10                  15

Val Leu Phe Ser Ala Pro Asn Cys Cys Ala Thr Asp Val Leu Gly Leu
            20                  25                  30

Ala Asp Leu Asp Cys Thr Thr Pro Pro Lys Val Pro Thr Ser Pro Xaa
            35                  40                  45

Asp Phe Gln
    50

<210> SEQ ID NO 3
```

-continued

```
<211> LENGTH: 30
<212> TYPE: PRT
<213> ORGANISM: F.poae
<220> FEATURE:
<221> NAME/KEY: MISC_FEATURE
<222> LOCATION: (1)..(18)
<223> OTHER INFORMATION: Xaa can be any naturally occurring amino acid
      other than cysteine
<220> FEATURE:
<221> NAME/KEY: MISC_FEATURE
<222> LOCATION: (20)..(28)
<223> OTHER INFORMATION: Xaa can be any naturally occurring amino acid
      other than cysteine

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Cys Xaa Xaa Xaa Xaa Xaa Xaa Xaa Xaa Cys Cys
            20                  25                  30

<210> SEQ ID NO 4
<211> LENGTH: 37
<212> TYPE: PRT
<213> ORGANISM: Nigrospora sp
<220> FEATURE:
<221> NAME/KEY: MISC_FEATURE
<222> LOCATION: (1)..(11)
<223> OTHER INFORMATION: Xaa can be any naturally occurring amino acid
      other than cysteine
<220> FEATURE:
<221> NAME/KEY: MISC_FEATURE
<222> LOCATION: (13)..(23)
<223> OTHER INFORMATION: Xaa can be any naturally occurring amino acid
      other than cysteine
<220> FEATURE:
<221> NAME/KEY: MISC_FEATURE
<222> LOCATION: (26)..(36)
<223> OTHER INFORMATION: Xaa can be any naturally occurring amino acid
      other than cysteine

<400> SEQUENCE: 4

Xaa Xaa Xaa Xaa Xaa Xaa Xaa Xaa Xaa Xaa Xaa Cys Xaa Xaa Xaa Xaa
1               5                   10                  15

Xaa Xaa Xaa Xaa Xaa Xaa Xaa Cys Cys Xaa Xaa Xaa Xaa Xaa Xaa Xaa
            20                  25                  30

Xaa Xaa Xaa Xaa Cys
            35

<210> SEQ ID NO 5
<211> LENGTH: 157
<212> TYPE: PRT
<213> ORGANISM: Unknown
<220> FEATURE:
<223> OTHER INFORMATION: by-product of Fusarium poae and Nigrospora sp
<220> FEATURE:
<221> NAME/KEY: MISC_FEATURE
<222> LOCATION: (1)..(38)
<223> OTHER INFORMATION: Xaa can be any naturally occurring amino acid
      other than cysteine; at most 2 Xaa's are present in locations 1-2,
      and Xaa may or may not be present in locations 3-38
<220> FEATURE:
<221> NAME/KEY: MISC_FEATURE
<222> LOCATION: (40)..(48)
<223> OTHER INFORMATION: Xaa can be any naturally occurring amino acid
      other than cysteine; at most 5 Xaa's are present in locations
      40-44, and Xaa may or may not be present in locations 45-48
```

```
<220> FEATURE:
<221> NAME/KEY: MISC_FEATURE
<222> LOCATION: (51)..(89)
<223> OTHER INFORMATION: Xaa can be any naturally occurring amino acid
      other than cysteine; at most 11 Xaa's are present in locations
      51-61, and Xaa may or may not be present in locations 62-89
<220> FEATURE:
<221> NAME/KEY: MISC_FEATURE
<222> LOCATION: (91)..(113)
<223> OTHER INFORMATION: Xaa can be any naturally occurring amino acid
      other than cysteine; at most 8 Xaa's are present in locations
      91-98, and Xaa may or may not be present in locations 99-113
<220> FEATURE:
<221> NAME/KEY: MISC_FEATURE
<222> LOCATION: (115)..(123)
<223> OTHER INFORMATION: Xaa can be any naturally occurring amino acid
      other than cysteine; at most 5 Xaa's are present in locations
      115-119, and Xaa may or may not be present in locations 120-123
<220> FEATURE:
<221> NAME/KEY: MISC_FEATURE
<222> LOCATION: (126)..(143)
<223> OTHER INFORMATION: Xaa can be any naturally occurring amino acid
      other than cysteine; at most 6 Xaa's are present in locations
      126-131, and Xaa may or may not be present in locations 132-143
<220> FEATURE:
<221> NAME/KEY: MISC_FEATURE
<222> LOCATION: (145)..(157)
<223> OTHER INFORMATION: Xaa can be any naturally occurring amino acid
      other than cysteine; at most 2 Xaa's are present in locations
      145-146, and Xaa may or may not be present in locations 147-157

<400> SEQUENCE: 5

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Cys Xaa Xaa Xaa Xaa Xaa Xaa Xaa Xaa
                35                  40                  45

Cys Cys Xaa Xaa Xaa Xaa Xaa Xaa Xaa Xaa Xaa Xaa Xaa Xaa Xaa
                50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Cys Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Cys Xaa Xaa Xaa Xaa Xaa Xaa Xaa Xaa Cys Cys Xaa Xaa Xaa
        115                 120                 125

Xaa Xaa Xaa Xaa Xaa Xaa Xaa Xaa Xaa Xaa Xaa Xaa Xaa Xaa Cys
        130                 135                 140

Xaa Xaa Xaa Xaa Xaa Xaa Xaa Xaa Xaa Xaa Xaa Xaa Xaa
145                 150                 155
```